United States Patent [19]

Mosbey

[11] Patent Number: 4,956,350
[45] Date of Patent: Sep. 11, 1990

[54] WOUND FILLING COMPOSITIONS

[75] Inventor: Deral T. Mosbey, St. Paul, Minn.

[73] Assignee: Minnesota Mining and Manufacturing Company, St. Paul, Minn.

[21] Appl. No.: 233,560

[22] Filed: Aug. 18, 1988

[51] Int. Cl.$^5$ .................... A61K 31/00; C08B 37/00; C08L 5/00
[52] U.S. Cl. ...................... 514/55; 514/925; 514/54; 536/20; 536/114; 106/162; 106/205
[58] Field of Search ............ 514/55, 54, 925; 536/20, 114; 106/162, 205

[56] References Cited

U.S. PATENT DOCUMENTS

| | | | |
|---|---|---|---|
| 3,903,268 | 9/1975 | Balassa | 424/180 |
| 4,394,373 | 7/1983 | Malette et al. | 424/95 |
| 4,501,835 | 2/1985 | Berke | 524/32 |
| 4,538,603 | 9/1985 | Pawelchak et al. | 128/156 |
| 4,570,629 | 2/1986 | Widra | 128/156 |
| 4,605,623 | 8/1986 | Malette et al. | 435/240 |
| 4,659,700 | 4/1987 | Jackson | 514/55 |

FOREIGN PATENT DOCUMENTS 0152898 8/1985 European Pat. Off. .
0187703 7/1986 European Pat. Off. .

OTHER PUBLICATIONS

Balassa et al., "Applications of Chitin and Chitosan in Wound–Healing Acceleration", pp. 296–305, in *Proceedings of the First International Conference on Chitin/Chitosan*, Ed. Muzzarelli et al., MIT Sea Grant Report MITSG 78-7, (May 1978).

*Primary Examiner*—Ronald W. Griffin
*Assistant Examiner*—Everett White
*Attorney, Agent, or Firm*—Donald M. Sell; Walter N. Kirn; Philip M. Goldman

[57] ABSTRACT

Wound filling compositions containing: (a) chitosan, (b) at least one compatible hydrocolloid material other than chitosan, and (c) water, exhibit a variety of properties desirable for use in filling large wound such as dermal ulcers, yet do not exhibit syneresis. Preferably compositions exhibit antimicrobial activity, would healing capability, a viscosity suitable to allow them to be applied to and remain in an open wound, and are able to absorb wound exudate.

10 Claims, No Drawings

WOUND FILLING COMPOSITIONS

TECHNICAL FIELD

The present invention relates to the field of wound treatment, and particularly to compositions that are applied to wounds such as dermal ulcers to allow or assist healing of the wound. In another aspect, the present invention relates to compositions and dressings containing the polysaccharide chitosan for application to wounds.

BACKGROUND ART

Many advances have been described in recent years for the treatment of dermal wounds, such as lacerations, incisions, burns, and sores. Such advances have addressed, for instance, the desirability of keeping the wound moist, yet not water-logged, keeping it free from microbial contamination, and so on. The treatment of wounds has evolved to the use of such things as inert dressings having nearly skin-like properties in terms of flexibility, moisture vapor transmission, low irritation, protection from infection, and so on.

In addition to inert dressings themselves, a variety of compounds, adjuvants, factors, and the like have been described that are either used alone or in conjunction with inert dressings, e.g., in order to provide antimicrobial activity, absorbancy, promote tissue regeneration, and so on. One approach involves the use of the polysaccharide chitin and its derivatives, particularly the deacetylated form chitosan, to enhance wound healing. U.S. Pat. No. 3,903,268, for example, describes wound healing compositions containing chitin, depolymerized chitin, or chitin derivatives.

U.S. Pat. No. 4,605,623 describes a method for cultivating myocytes in suspension involving the use of an aqueous chitosan solution sufficient to enable the three-dimensional growth of such myocytes and to inhibit undesired cells such as fibroblasts, tumor cells, mycoplasma and bacteria. U.S. Pat. No. 4,394,373 describes the use of chitosan, in liquid or powder form, to achieve hemostasis in wounds, vascular grafts, cardiac valves, and the like.

Wounds such as dermal ulcers pose a particular problem in terms of their treatment. Such wounds include, for instance, sores that are formed by the continual pressure of the body on underlying skin, an example being "bed sores", that often appear in patients confined for long periods of time in restricted positions. If not effectively treated, such wounds can become large, invasive, weeping sores that can progress so deeply so as to affect and even expose underlying tissues or bone. They often produce a large amount of exudate and can become a site of infection, including life-threatening infections.

A variety of approaches have been described for the treatment of dermal ulcers, some of which involve packing the open void with a dressing that is intended to generally conform to the space formerly occupied by normal tissue. Early approaches included the use of medicated gauze to pack such wounds. More recently, compositions having the ability to fill a deep wound and to absorb wound exudate have been used.

A commercially-available product, "Bard Absorption Dressing", available from C. R. Bard, Inc., Berkeley Heights, NJ, is sold as a dry powder for use in treating or packing wounds. This product is described as a "dry polysaccharide derivative made by graft copolymerization of carboxyl and carboxamide groups onto cornstarch", and is sold in a two-component pouch containing the dry powder in one portion and water in the other. The two components need to be mixed just before use. The resultant gel-like composition has a useful consistency. However, it absorbs water or exudate at a rapid rate and may desiccate the wound, thereby causing discomfort to the patient. Moreover, the composition does not provide antimicrobial activity or wound-healing properties, rather it is described as being "compatible with topical medications".

Other commercially available products include (1) "Spand-Gel Granulated Gel", available from Medi-Tech International Corp., Brooklyn, NY, which is described as a hydrogel composed of sterile water bound by polyacrylamide, and containing "cross-linked super absorbent poly-carbohydrate beads";

(2) "Debrisan ® Wound Cleaning Beads and Paste", available from Johnson & Johnson Co., New Brunswick, NJ, which is described as a mixture of polyethylene glycol with "spherical hydrophilic beads of dextranomer";

(3) "Pharmaseal HydraGran Absorbent Dressing", available from American Pharmaseal Co., Valencia, CA, which is described as being able to absorb up to 22 times its weight in human serum, and able to "trap bacterial contamination and necrotic debris"; and (4) "Geliperm wound management system", available from Geistlich-Pharma, Wolhusen, Switzerland, which is described as "an inert hydrogel formulation composed of sterile water bound by a polyacrylamide/agar network", and is available as both a smooth, transparent gel sheet and as a "granulate" having gel-like consistency.

It does not appear that any of the commercially-available products described above themselves contain ingredients having anti-microbial activity, although certain of the manufacturers claim to achieve an antimicrobial effect in various ways, e.g., by the physical removal of bacteria (by means of the suction force of an absorbent composition); by creating a physical barrier to the entry of bacteria, and so on.

Other dressings include "Hydra Gran Absorbent Dressing" (American General Health Care, Glendale, CA); "Wound Exudate Absorber" (Hollister, Inc., Libertyville, IL); "Duoderm Hydroactive Granules" (ConvaTec, Princeton, NJ); and "Comfeel Ulcus System" (Coloplast, Inc., Tampa, FL).

Yet other products are described in the patent literature. For instance, U.S. Pat. No. 4,538,603 describes, inter alia, the use of a granular product for packing a wound site, which can then be covered by the occlusive dressing described therein. Among the granular products described are water dispersible hydrocolloid materials such as sodium or calcium carboxymethylcellulose, pectin, gelatin, guar gum, locust bean gum, collagen, and karaya gum. Such materials are also included in the adhesive layers of the dressing itself. The purpose of these materials is described as providing "wet tack" between the dressing and the wound itself, thereby ultimately bonding the dressing to the skin.

Among the formulations that have been described for use in treating wounds such as dermal ulcers, are formulations containing chitin or its derivatives, although none appear to have gained wide commercial acceptance. Balassa et al., "Applications of Chitin and Chitosan in Wound-Healing Acceleration", pp. 296–305, in

*Proceedings of the First International Conference on Chitin/Chitosan,* Ed. Muzzarelli et al., MIT Sea Grant Report MITSG 78-7 (May 1978) describes the acceleration of healing in both "slow healing and non-healing wounds (ulcers)", by chitin, chitosan and depolymerized chitin.

U.S. Pat. No. 4,659,700 discloses gels or gel-like membranes prepared by dissolving chitosan in acid-water-glycerol solutions and then neutralizing the solutions with base. The gels are described as being useful carriers for a variety of other medicaments, but clearly would not themselves be very absorbent of wound exudate.

In each instance of which applicant is aware in which chitosan has been used with another polyelectrolyte to prepare a composition, the composition is either (1) not a homogeneous gel, e.g., is instead a dry, aqueous, or multiphasic (i.e., biphasic or greater) composition, or (2) is a gel or gel-like composition, but is formed by a separation, precipitation, or drying of the composition from a liquid phase, e.g., by what would be termed, for purposes of this discussion, "syneresis".

EPO Patent Application number 85101490 2, for instance, describes the preparation of capsules having a semipermeable membrane, and a liquid core which contains a biologically active material such as microbial cells. The capsules are formed, e.g., by the dropwise combination of an anionic polymer composition, such as alginate or carrageenan, with a cationic polymer composition, such as chitosan, where one of the compositions contains the active material. The resultant capsules contain a liquid core and are used in an aqueous medium.

In another example, described in U.S. Pat. No. 4,501,835, a polyacrylic acid/chitosan polyelectrolyte complex is prepared in aqueous acidic solution. A membrane or film can be formed by drying a coating of the complex.

Dry chitosan-containing compositions are described in EPO Patent Application no. 86300039.4, for a sustained release preparation containing (1) chitin, chitosan, or a mixture thereof, (2) at least one anionic polymer compound, and (3) at least one pharmaceutically active agent. These components are described as being in the form of "for example, tablets, granules, grains, powders, dental cones, films, or hard capsules."

In the only such instance to also involve the use of a chitosan/polyelectrolyte composition for wound healing, U.S. Pat. No. 4,570,629 describes hydrophilic biopolymeric copolyelectrolytes made up of: (a) a water-soluble linear anionic protein polyelectrolyte component derived from keratin, and (b) a water-soluble linear cationic biopolymer polyelectrolyte component. When the first component is contacted in the presence of water with the second component, "the components spontaneouslY rearrange themselves into a water-insoluble, water-swellable, solid coherent mass."

The cationic component is derived from at least one biopolymer selected from a glucosaminoglycan and collagen, and is described as including chitosan acetate, collagen acetate, and mixtures thereof. In their hydrated form, such copolyelectrolytes are described as stress-durable hydrogels that are useful as wound dressings.

It is clear that, to date, there still exists a need for a single composition that provides the properties desirable for an effective, versatile, wound filling material for use with wounds such as dermal ulcers, e.g. in terms of viscosity, absorbancy, antimicrobial activity, wound healing capability, ability to be effectively sterilized, and so on.

SUMMARY OF THE INVENTION

The present invention provides a wound-filling composition that exhibits several properties desired for the treatment of wounds such as dermal ulcers. Compositions of the present invention comprise:

(a) an amount of chitosan effective to promote healing and/or provide anti-microbial activity, (b) at least one compatible hydrocolloid material, other than chitosan, and (c) water, wherein the composition is a homogeneous gel having an initial viscosity suitable to allow it to be applied to and remain in a dermal ulcer, yet the composition is neither formed by nor exhibits syneresis.

Preferred compositions of the present invention provide a combination of properties not found in any other composition or dressing known to Applicant, including antimicrobial activity (i.e., microbiocidal and/or microbiostatic activity) and wound healing capabilities (e.g., increased rate of granulation and/or wound closing), largely conferred by virtue of the presence of chitosan, as well as suitable viscosity for their intended use, and the ability to absorb a sufficient amount of wound exudate, largely conferred by the presence of the compatible hydrocolloid material(s).

Preferred compositions of the present invention are gel-like compositions having a viscosity that enables them to be packed into wounds exhibiting large voids, such as dermal ulcers, even when such wounds are situated in inverted positions. The compositions remain in the wound, retain their integrity while in the wound, and are later easily removed from the site of the wound.

DETAILED DESCRIPTION

Wound-filling compositions of the present invention comprise:

(a) an amount of chitosan effective to promote healing and/or inhibit microbial growth, (b) at lease one compatible hydrocolloid material, other than chitosan, and (c) water wherein the composition is a homogeneous gel having an initial viscosity suitable to allow it to be applied to and remain in a dermal ulcer, yet the composition is neither formed by nor exhibits syneresis.

A preferred composition of the present invention has an initial viscosity suitable to allow it to be applied to and remain in a dermal ulcer; moreover, it does not exhibit syneresis at any point in time during its preparation, storage, or use; it has an absorbancy suitable to allow it to absorb a substantial amount of wound exudate without undue desiccation of the wound site; and it provides antimicrobial activity and wound healing capability to the wound site.

The term "wound filling composition" refers to a gel-like composition capable of substantially filling the void within a dermal ulcer. Such compositions are typically thereafter covered with a dressing, e.g., an occlusive dressing, to protect the area of the wound.

The term "dermal ulcer" as used herein, will be used interchangeably with the word "wound", and refers to an open lesion or break in the skin with loss of surface tissue, as with, for example, a decubitus ulcer or stasis ulcer.

The word "syneresis" as used herein, refers to the formation of a gel by contraction with an aqueous phase, as the contraction of a blood clot from serum, and/or to the contraction of a gel over time after its preparation, and the resultant separation of an aqueous phase from the gel. In particular, as used herein, the word refers to the separation of an aqueous phase from a wound filling composition to a degree where the composition would no longer be suitable for its intended purpose. A suitable test for syneresis is described more fully below.

The word "chitosan" as used herein refers to any form of chitin, chitosan, and deacetylated and/or depolymerized chitin that provides a desired combination of antimicrobial activity and wound healing capability to a composition of this invention. See, e.g., U.S. Pat. No. 4,394,373, the disclosure of which is incorporated herein by reference. Suitable forms of chitosan are commercially available, e.g., from Protan Laboratories, Inc. Redmond, WA, or can be prepared, e.g., by the method described in A. Domard and M. Rinando, Int. J. Biol. Macromol., 5:49 (1983). Preferred forms of chitosan are those readily soluble in water including, but are not limited to, chitosan salts such as chitosan malate and chitosan glutamate.

Chitosan is used at a final concentration that is effective to promote healing and/or inhibit microbial growth. Preferably chitosan is used at a final concentration of between about 0.1% and about 10% (by weight based on the weight of the composition). Particularly preferred are chitosan concentrations of between about 0.5% and about 5%. The term "wound healing" as used herein refers to the ability of chitosan to increase the rate at which granulation tissue forms and/or the rate a wound closes.

Compositions of the present invention also contain at least one compatible hydrocolloid material other than chitosan. The word "compatible" as used herein refers to a hydrocolloid material capable of being mixed in solution to achieve the desired viscosity, and to yield a composition that does not exhibit syneresis.

The term "hydrocolloid material" as used herein refers to a polymeric moiety or moieties that are capable of being mixed with chitosan in an aqueous system to form a gel that is both suitably absorbant, i.e., capable of attracting water, and of suitable viscosity for its intended use. The terms "gel" and "gel-like composition" as used herein refer to a composition that is of suitable viscosity for such purposes, e.g., a composition that is of a viscosity that enables it to be applied with a spatula and to remain in a dermal ulcer. The word "homogeneous" refers to a gel that does not contain discrete liquid or solid phases.

Hydrocolloid materials can be conveniently classified as either polycationic, polyanionic, or neutral. See, e.g., the disclosure of copending application U.S. Ser. No. 189,614, filed May 3, 1988, the disclosure of which is incorporated herein by reference. In addition to water, compositions of the present invention include chitosan, which itself can be classified as a polycationic hydrocolloid material, together with at least one other hydrocolloid material, i.e., a polycationic hydrocolloid material other than chitosan, or a polyanionic or neutral hydrocolloid material.

Suitable compatible hydrocolloid materials exhibit a desirable combination of such properties as biocompatibility, viscosity, absorbancy, and minimal adherence to moist wound tissue. Examples of suitable compatible hydrocolloid materials include, but are not limited to, polysaccharide gums.

Preferred hydrocolloid materials are those that are able to be directly mixed in solution with chitosan, i.e., those that can be readily combined in aqueous solution with chitosan so as to result in a composition that does not undergo syneresis.

The selection of preferred hydrocolloid materials can often by facilitated by evaluating the viscosity of a solution of the material itself. Preferred hydrocolloid materials are those that are both soluble in deionized water at a concentration of 1% (by weight), and that exhibit a viscosity at that concentration (24 hrs after preparation and at 25° C.) of at least about 1 poise as determined using a "Brookfield" viscometer, described more fully in the EXAMPLES below.

Examples of preferred compatible hydrocolloid materials are polysaccharide gums such as locust bean gum, karaya gum, tragacanth gum, guar gum and derivatives of guar gum such as hydroxypropyl guar (HP guar).

Hydrocolloid materials can be used alone or in combination with other compounds, e.g., other hydrocolloid materials. Certain hydrocolloid materials, e.g., karaya gum, tragacanth gum, and HP guar gum exhibit self-cohesive properties, such that at higher concentrations, they tend to impart a "stringy" characteristic to a composition of this invention, thereby making application of the composition to a wound difficult.

Other hydrocolloid materials, such as locust bean gum, impart a granular consistency to compositions of this invention, and have been found to decrease the, self-cohesive properties exhibited by other hydrocolloid materials. Although compositions can be prepared without locust bean gum, compositions containing locust bean gum are preferred, and particularly preferred are compositions containing locust bean gum in combination with karaya gum, tragacanth gum, and/or HP guar gum.

Hydrocolloid materials are present in the compositions of the present invention in a total amount sufficient to yield the desired absorbancy and viscosity. Preferably the hydrocolloid materials are present at a total final concentration of between about 5% and about 25% (by weight based on the weight of the final composition), and particularly preferred are compositions containing a total concentration of hydrocolloid materials of between about 10% and about 20% by weight.

A variety of optional ingredients can be included in compositions of the present invention, such as polypropylene glycol, glycerol, and other physiologically acceptable low molecular weight, e.g., less than about 3,000 molecular weight, polyols. Such ingredients may be useful, e.g., for facilitating the blending of compositions, controlling the adhesion of dressing for underlying tissue, and/or modifying the viscosity of a composition.

Compositions of the invention can also contain minor amounts of other ingredients such as antioxidants, deodorants, perfumes, antimicrobials, and other pharmacologically active agents available in the art.

Compositions of the present invention can be prepared, e.g., blended, using a variety of methods. See generally, Kirk-Othmer Encyclopedia of Chemical Technology, 3d ed., Vol. 15, "Mixing and Blending", pp. 604–637 (1981). The order of addition of the ingredients is not generally critical, although with mixers having lower shear, the addition of a surfactant such as glycerol or polypropylene glycol, e.g., at a final concentration of between about 1% to about 20% by weight, based on the weight of the composition, and preferably about 3% to about 10%, often aids in obtaining faster dispersion of the ingredients. Also with lower shear mixers, incremental additions of water to the ingredients often minimize lumping, and in turn, shorten the total mixing time.

Compositions of the present invention can be sterilized according to methods commonly used to sterilize compositions of a similar nature, e.g., methods that take care to avoid excessive pressure build-up in a closed container holding a water-based composition. Preferably, compositions of this invention are heat sterilized in an autoclave by an "air over pressure" method, wherein a composition of the invention is packaged in a heat sealed foil pouch that is able to withstand autoclave sterilization conditions, such as a pouch made from "Trilaminate" film, which is described as a laminated film of a polyester, foil and a modified polypropylene, and is available from Kapak Corp., St. Louis Park, MN.

Such "air over pressure" systems generally include a water spray cool down cycle, and are used to lessen the pressure differential between the pressure within the pouch and the pressure outside the pouch as the steam pressure in the autoclave is reduced. The air over pressure system maintains an autoclave chamber pressure of about 1.7 kg/cm$^2$ (5 psi) above the normal steam pressure, thus preventing pouch rupture. The water spray cool down cycle rapidly decreases the temperature and pressure inside the pouch, which also aids in preventing pouch rupture during the cool down cycle.

Whereas the viscosity of a 1% solution of a hydrocolloid material, as described earlier, is most conveniently determined by the use of a Brookfield viscometer, the viscosity of the composition after sterilization is generally too high to be determined by the use of a Brookfield viscometer, but can be determined by a variety of suitable techniques. Preferably viscosity is determined qualitatively, e.g., by evaluating compositions for the ability to be applied to and remain in a dermal ulcer. Particularly preferred are compositions that can be applied to and remain in such a wound even when the wound is in an inverted position, such as on the under side of a patient. In this manner, the least discomfort will be experienced by the patient during the application of the composition.

Viscosity can also be determined in a quantitative fashion. Preferably, viscosity of sterilized compositions is determined as a steady shear viscosity, using a parallel plate rheometer such as a Rheometrics Systems IV rheometer (Rheometrics, Inc., Piscataway, NJ) as described more fully in the EXAMPLES below.

When determined in this fashion, compositions of the present invention, after sterilization, e.g., by the air over pressure method of sterilization described herein, have an initial viscosity (i.e., before application to a wound) of between about $3\times10^4$ and about $2\times10^5$ poise. Preferred compositions have a viscosity of between about $5\times10^4$ and about $1.5\times10^5$ poise, and particularly preferred are compositions that have a viscosity of between about $6\times10^4$ and about $1\times10^5$ poise.

While syneresis is best determined qualitatively, as the visual separation of an aqueous phase from a gel to a degree where the gel would no longer be suitable for use as a composition of this invention, an indication of the tendency of a composition to undergo syneresis can be made as described in the EXAMPLES below.

Absorbancy can also be determined qualitatively, e.g., by evaluating the ability of the composition to absorb wound exudate, and comparing that to the ability of the composition to avoid unwanted desiccation of the wound site. At the same time, it is also important to consider the ability of the composition itself to retain its integrity and thereby to remain in the wound, as it absorbs exudate.

A semi-quantitative assessment of absorbancy can be made by placing a measured amount of the gel in the bottom of a tared jar, and spreading the gel out evenly over the bottom of the jar. Calf serum is added and the jar is closed, and left at ambient temperature for a predetermined time. Liquid is then decanted from above the gel and the jar and its contents are weighed. Any increase in weight is due to absorbed serum.

Suitable compositions of the present invention absorb between about 30 and about 150% of their weight, and preferably between about 70 and about 100%, when 10 g of calf serum is incubated with 4 g of a composition of this invention for 4 hours.

Compositions of the present invention can be packaged and stored according to conventional methods. Preferably such compositions are loaded, e.g., with a syringe, into foil pouches which are then heat sealed and sterilized.

After sterilization the compositions can be applied to a dermal ulcer by conventional means. For instance, a corner of the pouch containing such a composition is cut off and the composition is squeezed out directly into the wound. The composition can then be packed into the wound or patted down, e.g., with a sterile spatula or tongue depressor. The packed wound site may then be covered with a protective dressing, such as gauze or tape, or preferably with a contemporary skin-like dressing such as Tegaderm brand film dressing, 3M Company, St. Paul, Minnesota.

Compositions of the present invention can generally remain in a wound site for on the order of days, e.g., 2-days, at which time they may have absorbed a sufficient amount of exudate, and should be replaced with a fresh composition.

A particular advantage of the preferred compositions of the present invention is that preferred compositions are able to be removed from a wound site as an intact "plug", and also that any residue left behind after removal of such a plug can be easily removed by routine methods, e.g., irrigation of the wound, such as irrigation using the pressure exerted by a fluid delivered through a 19 gauge needle by a 35 ml syringe under hand pressure. See generally, T. Hunt and J. Dunphy, eds., pp. 408–413, in "Fundamentals of Wound Management", Appleton-Century-Crofts, NY, 1979.

This invention is further illustrated by the following EXAMPLES, but the particular materials and amounts thereof recited in these EXAMPLES, as well as other conditions and details, should not be construed to unduly limit this invention. Unless otherwise indicated, all amounts are expressed as a percent, based on weight, of the ingredient compared to the composition as a whole.

EXAMPLES

EXAMPLE 1

Preparation of a Wound-filling Gel

Water (168 g) was charged to a blender (Waring). Polypropylene glycol (10 g), chitosan malate (2 g), HP guar gum (6 g) (Hi-Tek Polymers, Inc., Louisville, KY) and locust bean gum (14 g) (Hi-Tek Polymers) were added. The mixture was blended until a smooth consistency was attained (about 10 minutes). The resulting gel-like composition was sterilized by an air over pressure method at 118° C. (245° F.) for 52 minutes in an autoclave equipped with an air over pressure mechanism without apparent deterioration or syneresis.

The resulting composition was cream colored, thick, and paste-like. It had a steady shear viscosity of $6.2 \times 10^4$ poise, as determined on a parallel plate rheometer as described in EXAMPLE 2 below, and a physiologically acceptable pH of approximately 4.8.

EXAMPLE 2

Identification of Suitable Hydrocolloid Materials, and Preparation of Gels Therefrom The hydrocolloid materials listed in TABLE 1 were prepared as 1% (by weight) solutions in deionized water and were evaluated for Brookfield viscosity using a Brookfield Model LVT viscometer (Brookfield Engineering Laboratories, Inc., Stoughton, MA) at 30 rpm and 23° C. Each of the hydrocolloid materials are polysaccharide gums and were obtained from Sigma Chemical Co., St Louis, MO, except for dextran (Pharmacia, Inc., Piscataway NJ), and locust bean gum and HP guar gum (Hi-Tech Polymers).

Those materials exhibiting a viscosity greater that about 1 poise when prepared in this manner were then visually evaluated for evidence of syneresis when mixed with chitosan as described below, the results of which evaluation are also listed in TABLE 1.

Syneresis was evaluated by mixing 12 g of the hydrocolloid to be evaluated with 6 g of chitosan malate in a laboratory blender (Waring) with 182 g deionized water. Blending was continued for about 5 minutes, to obtain a smooth, well-dispersed gel. The gel (8 g) was transferred to a 10 ml closed vial and placed in an oven at 38° C. (100° F.) for 3 days. The gel was then visually inspected for the presence of an aqueous phase.

For purposes of the present EXAMPLE, hydrocolloid materials having a viscosity of greater than about 1 poise in a 1% solution and exhibiting no visual formation of an aqueous phase when mixed with chitosan to form a composition under the above conditions, i.e., no syneresis at all, are identified in TABLE 1 and were used below. Generally, suitable compositions of the present invention exhibit about 10% or less syneresis (i.e., about 10% or less of the original weight of the gel appears as an aqueous phase after 3 days at 38° C.). Preferred compositions exhibit about 5% or less syneresis, and particularly preferred are compositions that exhibit about 1% or less syneresis.

TABLE 1

| Hydrocolloid Material | Viscosity at 1% (poise) | Syneresis |
| --- | --- | --- |
| Storax | insoluble | |
| Damar Grade I | insoluble | |
| Pontianak | insoluble | |
| Elemi | insoluble | |
| Mastic | insoluble | |
| Rosin | insoluble | |
| Damar Grade II | insoluble | |
| Guaiac | insoluble | |
| Accroides | insoluble | |
| Dextran | 0.03 | |
| Ghatti | 0.042 | |
| Arabic | 0.03 | |
| Agar | 0.01 | |
| Carrageenan Type I | 1.14 | yes |
| Locust Bean | 1.45 | no |
| Tragacanth | 2.40 | no |
| Karaya | 4.50 | no |
| Xanthan | 18.40 | yes |
| Carrageenan Type II | 29.20 | yes |
| HP Guar | 30.00 | no |
| Guar | 35.50 | no |

Compositions having the ingredients listed below in TABLE 2 were prepared by blending, as described in EXAMPLE 1. "PPG" refers to polypropylene glycol, obtained from Union Carbide Corp. The compositions were then sterilized by an air over pressure method at 118° C. for 52 minutes and evaluated for steady shear viscosity on a parallel plate rheometer at the following conditions:

Test: steady rate sweep
Test geometry: parallel plate
Gap: 1.5 mm
Diameter: 25 mm
Stabilization time before measurement: 0.3 min.
Shear rate range: $1 \times 10^3$ to 10.0 sec$^{-1}$
Chart recorder speed: 1 cm/min.
Chart recorder span: 1 volt

TABLE 2

| | Gel Compositions (in parts) | | | | | | | |
| --- | --- | --- | --- | --- | --- | --- | --- | --- |
| Sample No. | Chitosan Malate | HP Guar | Locust Bean | Karaya | Tragacanth | PPG | Water | Steady Shear Viscosity (poise) |
| 1 | 2 | | 14 | | 6 | 10 | 168 | $2.4 \times 10^4$ |
| 2 | 2 | 6 | 10 | | | 10 | 172 | $2.6 \times 10^4$ |
| 3 | 2 | | 14 | 20 | | 10 | 154 | $3.4 \times 10^4$ |
| 4 | 2 | | 14 | 8 | | 10 | 166 | $3.4 \times 10^4$ |
| 5 | 2 | | 14 | | 8 | 10 | 166 | $3.4 \times 10^4$ |
| 6 | 2 | | 14 | 6 | | 10 | 168 | $3.7 \times 10^4$ |
| 7 | 2 | 10 | 8 | | | 10 | 170 | $4.1 \times 10^4$ |
| 8 | 2 | 4 | 14 | | | 10 | 170 | $4.8 \times 10^4$ |
| 9 | 2 | | 14 | 20 | | 10 | 154 | $5.5 \times 10^4$ |
| 10 | 2 | 4 | 16 | | | 10 | 168 | $5.9 \times 10^4$ |
| 11 | 2 | 6 | 14 | | | 10 | 168 | $6.2 \times 10^4$ |
| 12 | 2 | 10 | 10 | | | 10 | 168 | $6.7 \times 10^4$ |
| 13 | 2 | 4 | 18 | | | 10 | 166 | $8.5 \times 10^4$ |
| 14 | 2 | 10 | 14 | | | 10 | 164 | $1.1 \times 10^5$ |
| 15 | 2 | 20 | 6 | | | 10 | 162 | $1.5 \times 10^5$ |
| 16 | 2 | 6 | 20 | | | 10 | 162 | $1.2 \times 10^5$ |
| 17 | 2 | 20 | 8 | | | 10 | 160 | $1.8 \times 10^5$ |
| 18 | 2 | 26 | 10 | | | 10 | 152 | $2.4 \times 10^5$ |

As seen from the results in TABLE 2, compositions can be prepared using a variety of types, combinations and concentrations of hydrocolloid materials, and having a broad range of viscosities, without exhibiting syneresis. It was observed that sample numbers 1–3 were not viscous enough to be suitable for use in packing a wound; sample numbers 4–8 were on the lower borderline of suitable viscosity; sample numbers 9–15 were very suitable; and sample numbers 16–18 were on the upper borderline of viscosity for such use.

EXAMPLE 3

Effect of PPG

A composition as described in sample 11, TABLE 2 of EXAMPLE 2 was prepared with and without PPG. The results, set forth below in TABLE 3, indicate that both samples perform similarly. The presence of the PPG appears to aid in the blending of the compositions however, particularly when low shear, production-type, mixers are used. Thorough mixing in such a mixer can take on the order of 12 hours if no PPG is added, yet on the order of one hour or less if PPG is added at a concentration of about 5%.

TABLE 3

| | Gel Compositions (in parts) | | | | | | |
|---|---|---|---|---|---|---|---|
| Sample No. | Chitosan Malate | HP Guar | Locust Bean | PPG | Water | Steady Shear Viscosity (poise) | pH | Absorbency (%) |
| 1 | 2 | 6 | 14 | 10 | 168 | $6.2 \times 10^4$ | 4.4 | 92 |
| 2 | 2 | 6 | 14 | — | 178 | $6.3 \times 10^4$ | 4.4 | 79 |

EXAMPLE 4

Antimicrobial Effectiveness

Compositions containing increasing amounts of chitosan were prepared in the manner described in EXAMPLE 2, in order to determine the effectiveness of chitosan in providing anti-microbial activity. Such compositions were compared to a commercially available wound filling material, "Bard Absorption Dressing", available from C. R. Bard, Inc., Berkeley Heights, NJ, which was prepared according to its directions.

Compositions were prepared containing 3% HP guar gum, 7% locust bean gum, 5% PPG, and the concentration of chitosan malate set forth below in TABLE 4.

One (1) gram samples of each composition were placed in sterile fritted glass tissue grinders with 3 ml of a bacterial inoculum of Streptococcus faecalis, and mixed to form a viscous fluid. 100 mg samples were removed and diluted with 9.9 ml of sterile saline. Culture plates were then prepared with "M - enterococcus medium" (BBL, Becton Dickinson, Cockeysville, MD) at various dilutions and were incubated at 35° C. for 24 hours. The cell count on each plate was then determined using a Biotran II Automatic Colony Counter (New Brunswick Scientific Co., Inc., Edison, NJ). The initial inoculum was determined to be approximately $2.1 \times 10^5$ Colony Forming Units ("CFU") per ml.; therefore the CFU expected were the cell count to remain constant (i.e., no cell replication or death) in each sample would be approximately $1.6 \times 10^3$ CFU.

The results in TABLE 4 indicate the microbiostatic and/or microbiocidal effectiveness of increasing chitosan malate concentrations. Under the, conditions tested, a static level of cell growth was seen beginning with a 0.5% concentration of chitosan, and a 10% concentration was sufficient to prevent all cell growth. Concentrations of less than 0.5%, e.g., down to about 0.1% or less, may be effective under other conditions, or for other purposes, such as wound healing, and concentrations higher than 10%, e.g., up to about 15%, can be suitably prepared and used. The Bard product did not exhibit either a microbiostatic or microbiocidal effect.

TABLE 4

| Sample | Chitosan Malate (%) | Cell Count (CFU) |
|---|---|---|
| 1 | 0.1 | $1.9 \times 10^7$ |
| 2 | 0.5 | $4.9 \times 10^3$ |
| 3 | 1.0 | $7.6 \times 10^3$ |
| 4 | 5.0 | $2.0 \times 10^3$ |
| 5 | 10.0 | 0 |
| 6 | 15.0 | 0 |
| Bard | — | $1.8 \times 10^6$ |

EXAMPLE 5

Subjective Evaluation

A composition prepared as described in Sample 11 of EXAMPLE 2 was used to fill experimentally induced wounds in pig skin. This composition is a translucent, petroleum jelly-colored gel, that has a slight yeast-like odor, a dull sheen, and a rough or almost granular appearance. It is somewhat sticky to the touch, leaving a slight moist residue on the finger, but is conformable in that it can be formed into a shape and generally retain that shape.

A standard wound model was used, using the shaved backs of 30–45 kg Yorkshire pigs. Wounds of approximately 2.5 cm × 2.5 cm (1 in. × 1 in.) were made with a #2 scalpel blade, cutting down to the fascia. The wounds were filled with the composition to the outer layer of the surrounding epidermis. An outer covering of either an occlusive dressing, a hydrocolloid dressing, or gauze was used.

Clinical nurses were asked to use the composition to fill a wound, using a spatula. It was found that the composition handled well, particularly in terms of its consistency; it maintained its integrity in the wound, and could generally be later removed from the wound as an intact plug. Intact removal as a plug made it easier to remove the residue from the wound site by simple irrigation, using saline from a 35 cc syringe having a 19 gauge needle.

What is claimed is:

1. A wound-filling composition comprising:
  (a) An amount of chitosan effective to promote healing or provide anti-microbial activity, or both,
  (b) at least one compatible hydrocolloid material, other than chitosan, and
  (c) water wherein said composition is a homogeneous gel having an initial viscosity suitable to allow it to be applied to and remain in a dermal ulcer, yet said composition is neither formed by nor exhibits syneresis.

2. A composition according to claim 1 wherein said composition has an initial steady shear viscosity of between about $3 \times 10^4$ and about $2 \times 10^5$ poise.

3. A composition according to claim 1 wherein said chitosan is present at a concentration of between about 0.1% and about 10% by weight based on the weight of said composition.

4. A composition according to claim 1 wherein said hydrocolloid material is present at a total concentration of between about 5% and about 25% by weight based on the weight of said composition.

5. A composition according to claim 1 wherein said hydrocolloid material comprises a polysaccharide gum.

6. A composition according to claim 5 wherein said polysaccharide gum is selected from a group consisting of locust bean gum, karaya gum, tragacanth gum, guar gum, and hydroxylpropyl guar gum.

7. A composition according to claim 1 wherein said composition exhibits absorbancy of wound exudate.

8. A composition according to claim 7 wherein said composition is able to absorb between about 30% and about 50% of its weight without substantial deterioration of the composition.

9. A composition according to claim 1 further comprising an adjuvant selected from the group consisting of polypropylene glycol, glycerol, and low molecural weight polyols.

10. A method of treating a wound comprising applying to the wound a composition comprising:
  (a) an amount of chitosan effective to promote healing or provide anti-microbial activity, or both,
  (b) at least one compatible hydrocolloid material, other than chitosan, and
  (c) water wherein said composition is a homogeneous gel having an initial viscosity suitable to allow it to be applied to and remain in said wound, yet said composition is neither formed by nor exhibits syneresis.

* * * * *